US00PP16259P2

(12) United States Plant Patent
Bartels

(10) Patent No.: US PP16,259 P2
(45) Date of Patent: Feb. 14, 2006

(54) ***PHLOX* PLANT NAMED 'BARTWENTYNINE'**

(50) Latin Name: *Phlox paniculata*
Varietal Denomination: Bartwentynine

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 22 days.

(21) Appl. No.: 11/041,623

(22) Filed: Jan. 22, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Bartwentynine', characterized by its upright and compact plant habit; freely branching growth habit; white-colored flowers; freely flowering habit; and good garden performance.

2 Drawing Sheets

Bontanical designation: *Phlox paniculata.*
Cultivar denomination: 'Bartwentynine'.

BACKGROUND OF THE INVENTION

The present Invention relates to a new and distinct cultivar of *Phlox* plant, botanically known as *Phlox paniculata,* and hereinafter referred to by the cultivar name Bartwentynine.

The new *Phlox* is a product of a planned breeding program conducted by the Inventor in Aalsmeer, The Netherlands. The objective of the breeding program was to create new compact pot-type *Phlox* cultivars with numerous flowers with attractive leaf and flower coloration.

The new *Phlox* originated from a cross-pollination made by the Inventor in Aalsmeer, The Netherlands of two unnamed selections of *Phlox paniculata,* not patented. The new *Phlox* was discovered and selected by the Inventor as a flowering plant within the progeny of the stated cross-pollination in a controlled environment in Aalsmeer, The Netherlands.

Asexual reproduction of the new cultivar by terminal cuttings in Aalsmeer, The Netherlands, has shown that the unique features of this new *Phlox* are stable and reproduced true to type in successive generations.

SUMMARY OF THE INVENTION

Plants of the cultivar Bartwentynine have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Bartwentynine'. These characteristics in combination distinguish 'Bartwentynine' as a new and distinct cultivar:

1. Upright and compact plant habit.
2. Freely branching growth habit.
3. White-colored flowers.
4. Freely flowering habit.
5. Good garden performance.

Plants of the new *Phlox* differ from plants of the female and male parent selections in flower coloration. In addition, plants of the new *Phlox* are more compact than plants of the male parent selection.

Plants of the new *Phlox* can be compared to plants of the *Phlox paniculata* cultivar Barten, disclosed in U.S. Plant Pat. No. 11,802. In side-by-side comparisons conducted in Aalsmeer, The Netherlands, plants of the new *Phlox* differed from plants of the cultivar Barten primarily in flower color as plants of the cultivar Barten had lavender-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox.*

The photograph on the first sheet comprises a side perspective view of a typical flowering plant of 'Bartwentynine' grown in a container.

The photograph on the second sheet is a close-up view of typical flowers of 'Bartwentynine'.

DETAILED BOTANICAL DESCRIPTION

The aforementioned photographs, following observations and measurements describe plants grown in Aalsmeer, The Netherlands, in a glass-covered greenhouse and under commercial production practices during the summer. Plants were about three months old when the photographs and description were taken. During the production of the plants, day temperatures ranged from 18 to 28° C. and night temperatures ranged from 10 to 18° C. In the following description, color references are made to The Royal Horticultural Society Colour Chart, 1995 Edition, except where general terms of ordinary dictionary significance are used.

Botanical classification: *Phlox paniculata* cultivar Bartwentynine.

Parentage:

*Female parent.*—Unnamed selection of *Phlox paniculata,* not patented.

*Male parent.*—Unnamed selection of *Phlox paniculata,* not patented.

Propagation:

*Type cutting.*—Vegetative cuttings.

*Time to initiate roots, summer.*—About three weeks at 18° C.

*Time to initiate roots, winter.*—About five weeks at 18° C.

*Time to produce a rooted young plant, summer.*—About four weeks at 18° C.

*Time to produce a rooted young plant, winter.*—About six weeks at 18° C.

*Root description.*—Thick, fibrous.

*Rooting habit.*—Freely branching; moderately dense.

Plant description:

*Plant form/habit.*—Upright and compact plant habit; narrow inverted triangle. Freely branching with about ten lateral branches per plant.

*Plant height.*—About 45 cm.

*Plant width* (*spread*).—About 35 cm.

*Lateral branches.*—Length: About 10 cm. Diameter: About 3 mm. Internode length: About 1.5 cm. Strength: Strong. Texture: Smooth, glabrous. Color: Close to 146A.

*Foliage description.*—Arrangement: Alternate, simple; sessile. Length: About 8 cm. Width: About 4 cm. Shape: Oblong to elliptic. Apex: Acuminate. Base: Rounded. Margin: Entire. Texture, upper and lower surfaces: Smooth, glabrous; leathery. Venation pattern: Pinnate. Color: Developing leaves, upper surface: 143A. Developing leaves, lower surface: 144A. Fully expanded leaves, upper surface: 137A. Fully expanded leaves, lower surface: 138A. Venation, upper surface: 137A. Venation, lower surface: 138A.

Flower description:

*Flower type/habit.*—Single, rounded salverform flowers arranged in terminal panicles; panicles globular to pyramidal in form; flowers face upright and outward. Freely flowering habit with about 24 to 36 flower buds and flowers per panicle.

*Fragrance.*—Typical of species.

*Natural flowering season.*—Continuously flowering from spring through fall in The Netherlands. Flowers not persistent.

*Postproduction longevity.*—Flowers last about four days on the plant.

*Flower buds.*—Height: About 1 cm. Diameter: About 5 mm. Shape: Elliptic. Color: 155A.

*Flower diameter.*—About 2 cm.

*Petals.*—Quantity per flower: Typically five in a single whorl; petals fused at the base into a narrow tube. Length (including tube): About 2.5 cm. Width: About 1 cm. Shape: Obovate. Apex: Broadly acute. Margin: Entire. Aspect: Mostly flat. Texture, upper and lower surfaces: Smooth, glabrous; satiny. Color: Developing petals, upper and lower surfaces: 155A. Fully expanded petals, upper and lower surfaces: 155A. Throat: 155A. Tube: 155A.

*Sepals.*—Quantity per flower: Typically five in a single whorl, fused; narrow tubular calyx. Length: About 5 mm. Width: About 1 mm. Shape: Narrowly deltoid. Apex: Acuminate. Texture, upper and lower surfaces: Smooth, glabrous. Color, upper and lower surfaces: 144A.

*Pedicels.*—Length: About 1 cm. Diameter: About 1.5 mm. Orientation: Upright to about 45° from vertical. Strength: Strong. Color: 145A.

*Reproductive organs.*—Stamens: Quantity per flower: Typically five. Anther shape: Oblong. Anther length: About 1 mm. Anther color: 2D. Pollen amount: Scarce. Pollen color: 15A. Pistils: Quantity per flower: Typically one. Pistil length: About 2.5 cm. Stigma shape: Tri-parted. Stigma color: 154D. Style length: About 2.5 cm. Style color: 154D. Ovary color: 144A.

Disease/pest resistance: Plants of the new *Phlox* have been noted to be resistant to Powdery Mildew. Plants of the new *Phlox* have not been noted to be resistant to other pathogens and pests common to *Phlox.*

Garden performance: Plants of the new *Phlox* have been observed to have good garden performance and tolerate rain, wind and temperatures ranging from 0 to about 35° C.

It is claimed:

1. A new and distinct cultivar of *Phlox* plant named 'Bartwentynine', as illustrated and described.

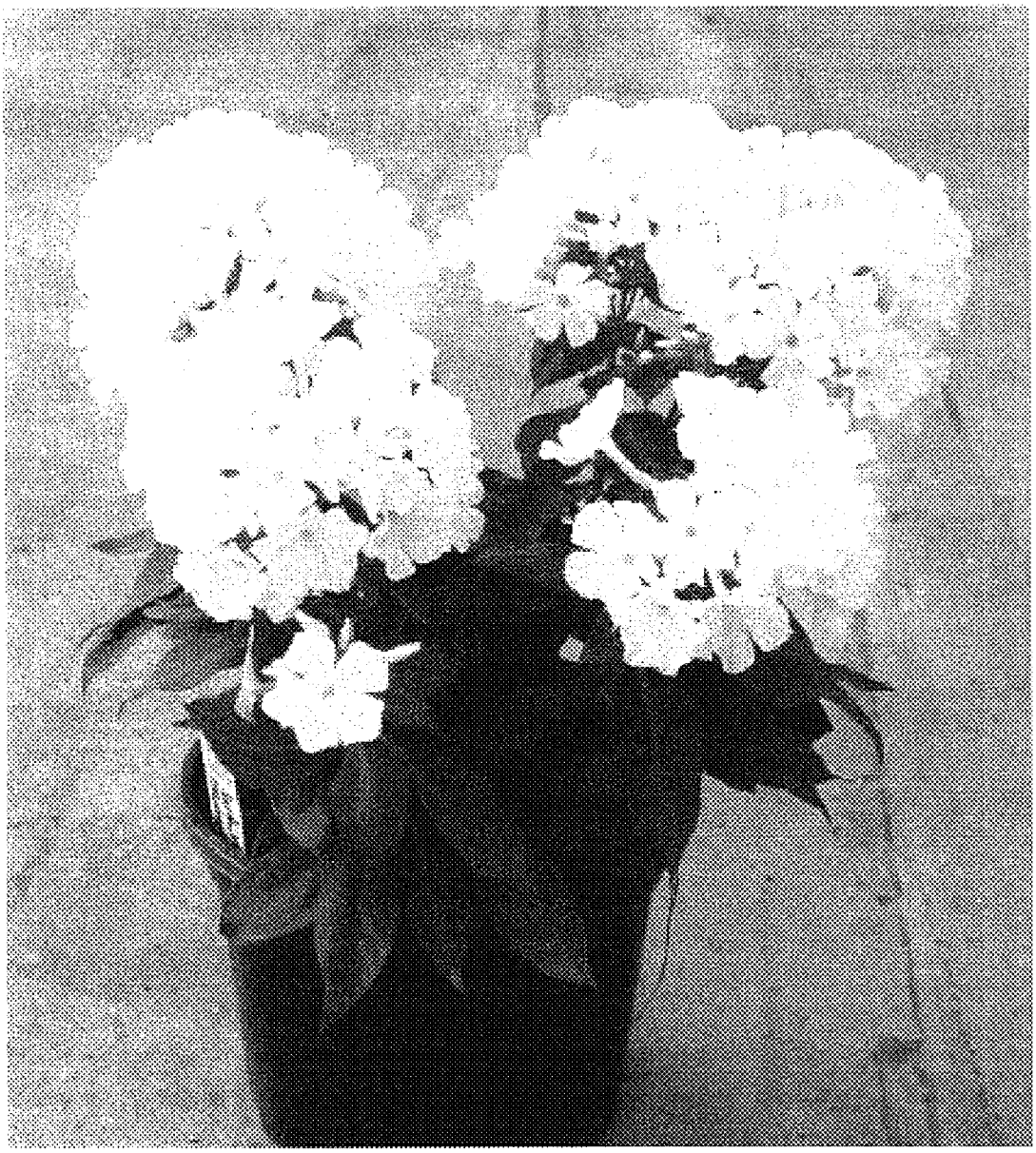

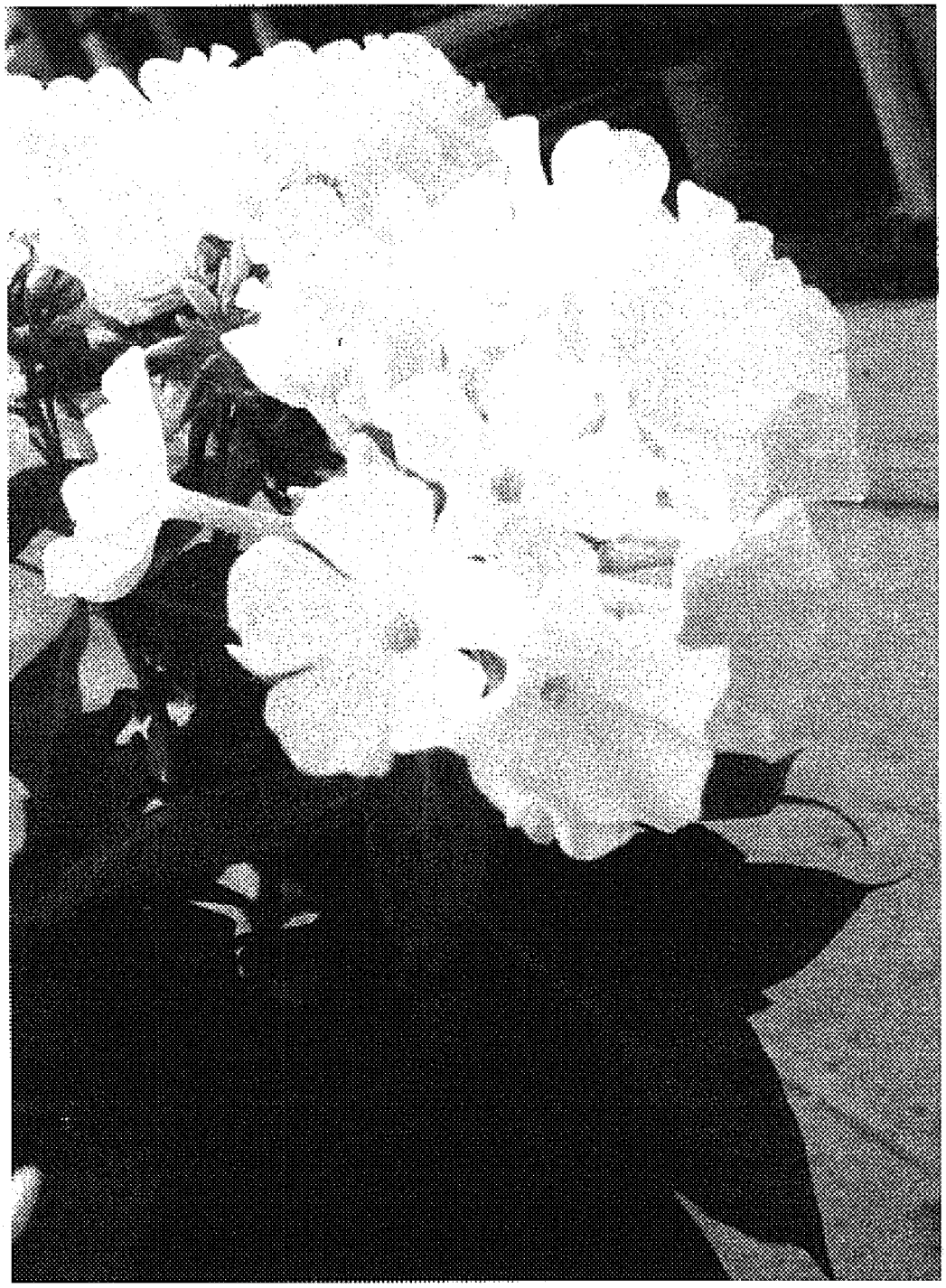

* * * * *